(12) United States Patent
Mathiowitz et al.

(10) Patent No.: US 8,776,802 B2
(45) Date of Patent: Jul. 15, 2014

(54) METHODS AND SYSTEMS FOR PROLONGED LOCALIZATION OF DRUG DELIVERY

(75) Inventors: Edith Mathiowitz, Brookline, MA (US); Bryan Laulicht, Great Neck, NY (US)

(73) Assignee: Brown University, Providence, RI (US)

( * ) Notice: Subject to any disclaimer, the term of this patent is extended or adjusted under 35 U.S.C. 154(b) by 208 days.

(21) Appl. No.: 13/217,883

(22) Filed: Aug. 25, 2011

(65) Prior Publication Data
US 2012/0053451 A1     Mar. 1, 2012

Related U.S. Application Data

(60) Provisional application No. 61/376,797, filed on Aug. 25, 2010.

(51) Int. Cl.
*A61B 5/05*     (2006.01)
*A61K 9/48*     (2006.01)

(52) U.S. Cl.
USPC ............................................... 128/899; 600/9

(58) Field of Classification Search
USPC ....................... 128/897–899; 600/9
See application file for complete search history.

(56) References Cited

U.S. PATENT DOCUMENTS

| | | | | |
|---|---|---|---|---|
| 5,753,477 | A * | 5/1998 | Chan | 435/455 |
| 2002/0198470 | A1 * | 12/2002 | Imran et al. | 600/587 |
| 2006/0152309 | A1 * | 7/2006 | Mintchev et al. | 335/58 |
| 2006/0155174 | A1 * | 7/2006 | Glukhovsky et al. | 600/301 |
| 2008/0063703 | A1 * | 3/2008 | Gross et al. | 424/463 |
| 2008/0193543 | A1 | 8/2008 | Morello, III et al. | |
| 2008/0207999 | A1 * | 8/2008 | Abraham-Fuchs et al. | 600/118 |
| 2009/0287036 | A1 | 11/2009 | Shapiro et al. | |
| 2010/0286668 | A1 * | 11/2010 | Tanaka et al. | 604/891.1 |

OTHER PUBLICATIONS

Arruebo et al. "Magnetic nanoparticles for drug delivery" Nanotoday, 2007, vol. 2, pp. 22-32.
Brainerd et al. "X-Ray Reconstruction of Moving Morphology (XROMM): Precision, Accuracy and Applications in Comparative Biomechanics Research" J Exp Zool, 2010, vol. 313A, pp. 262-279.
Chen et al. "Magnetically-responsive polymerized liposomes as potential oral delivery vehicles" Pharm Res, 1997, vol. 14, pp. 537-540.
Davis "Formulation strategies for absorption windows" Drug Disc Today, 2005, vol. 10, pp. 249-257.
Edelman et al. "Controlled and modulated release of basic fibroblast growth factor" Biomaterials, 1991, vol. 12, pp. 619-626.
Ferens et al. "Motor patterns and propulsion in the rat intestine in vivo recorded by spatio-temporal maps" Neurogastro Motil, 2005, vol. 17, pp. 714-720.

(Continued)

*Primary Examiner* — Christine Matthews
*Assistant Examiner* — Joshua D Lannu
(74) *Attorney, Agent, or Firm* — Lawson & Weitzen LLP; Sonia K. Guterman; Preeti T. Arun

(57) ABSTRACT

An effective method for prolonging localization of therapeutics within the rat gastrointestinal tract of at least about 12 hours is provided. Attractive forces between an orally administered magnetic dose and an external magnet were monitored and internal dose motion in real time using biplanar videofluoroscopy was visualized. Tissue elasticity was quantified as a measure of tissue health by combining data streams. The methods address safety, efficacy, and monitoring capacity of magnetically localized doses and show a platform for testing the benefits of localized drug delivery.

18 Claims, 15 Drawing Sheets

(56) References Cited

OTHER PUBLICATIONS

Goldberg et al. "Challenges for the oral delivery of macromolecules" Nat Rev, 2003, vol. 2, pp. 289-295.

Groning et al. "Acyclovir serum concentrations following peroral administration of magnetic depot tablets and the influence of extracorporal magnets to control gastrointestinal transit" Eur J Pharm Biopharm, 1998, vol. 46, pp. 285-291.

Guignet et al. "Magnet Tracking: a new tool for in vivo studies of the rat gastrointestinal motility" Neurogastro Motil, 2006, vol. 18, pp. 472-478.

Hedrick "Software techniques for two- and three-dimensional kinematic measurements of biological and biomimetic systems" Bioinsp Biomim, 2008, vol. 3, pp. 1-6.

Ito et al. "Magnetic granules: a novel system for specific drug delivery to esophageal mucosa in oral administration" Intl J Pharm, 1990, vol. 61, pp. 109-117.

Langer "Drug delivery and targeting" Nature, 1998, vol. 392, pp. 5-10.

Laulicht et al. "Understanding gastric forces calculated from high-resolution pill tracking" Proc Natl Acad Sci, 2010, vol. 107, pp. 8201-8206.

Mathiowitz et al. "Biologically erodable microspheres as potential oral drug delivery systems" Nature, 1997, vol. 386, pp. 410-414.

Polyak et al. "Magentic targeting for site-specific drug delivery: applications and clinical potential" Expert Opin Drug Deliv, 2009, vol. 6, pp. 53-70.

Riskin et al. "Qualifying the complexity of bat wing kinematics" J Theor Biol, 2008, vol. 254, pp. 604-615.

Teply et al. "The use of charge-coupled polymeric microparticles and micromagnets for modulating the bioavailability of orally delivered macromolecules" Biomaterials, 2008, vol. 29, pp. 1216-1223.

Whitehead et al. "Oral delivery of macromolecules using intestinal patches: applications for insulin delivery" J Control Release, 2004, vol. 98, pp. 37-45.

Widder et al. "Tumor remission in Yoshida sarcoma-bearing rats by selective targeting of magnetic albumin microspheres containing doxorubicin" Proc Natl Acad Sci, 1981, vol. 78, pp. 579-581.

\* cited by examiner

METHODS AND SYSTEMS FOR PROLONGED LOCALIZATION OF DRUG DELIVERY

RELATED APPLICATIONS

The present utility application claims the benefit of U.S. provisional application Ser. No. 61/376,797 filed Aug. 25, 2010, which is hereby incorporated herein by reference in its entirety.

TECHNICAL FIELD

This invention relates to a magnetic device used for localized treatment of internal diseases and disorders.

BACKGROUND

Gastrointestinal (GI), urogenital, and respiratory illnesses remain major public health problems. In the United States alone, about 650,000 persons are diagnosed with GI tract and urogenital cancers (tongue, esophageal, gastric, small intestine, colorectal, anal, bladder, pancreatic, kidney/renal, prostate, testicular, cervical and ovarian cancers) each year, resulting in about 200,000 deaths. Another 40 million are diagnosed with respiratory illnesses such as pneumonia, lung cancer, asthma, bronchitis, emphysema, and cystic fibrosis. Food poisoning incidence from all causes is about 76 million resulting in about 5,000 deaths. Other GI tract disorders such as inflammatory bowel disease, including ulcerative colitis and Crohn's disease, affect 1.4 million Americans.

Current treatments are insufficient for many of these diseases and disorders. Increased residence time in a particular region of the gastrointestinal (GI) tract would greatly improve the therapeutic benefit of many orally administered pharmaceuticals[1]. Controlling GI residence may also provide oral administration of therapeutics that currently are administered by injection[2-6] a benefit for cost savings and comfort of those affected by these diseases.

SUMMARY

An embodiment of the invention herein provides an apparatus for controlling residence and duration of a therapeutic agent in an anatomic location of a subject, the apparatus including an internal magnet and an external magnet, such that the internal magnet exerts a force towards the external magnet, such that the force is regulated by a distance between the internal magnet and the external magnet to control stress to a tissue in an area of the anatomic location, a therapeutic agent, optionally formulated in a drug delivery component; and a capsule for containing the internal magnet and therapeutic agent, thereby including a magnetic pill.

A related embodiment of the apparatus has the capsule as a soluble capsule, for example, a gelatin capsule, for release of the agent. An alternative embodiment of the apparatus has the capsule which is insoluble and functions as an osmotic pump for release of the agent, for example, an insoluble capsule made of cellulose acetate, ethyl cellulose, or an acrylic resin such as polymethyl acrylate resin.

In a related embodiment of the apparatus, presence of the internal magnet at the anatomic location exerts minimal stress force applied to tissue of the location. In a related embodiment of the apparatus the internal magnet has field strength of at least about 0.1 Tesla and less than about 4 Tesla. A related embodiment of the apparatus provides the internal magnet with a field strength of less than about 4 Tesla, less than about 3.5 Tesla, less than about 3 Tesla, less than about 2.5 Tesla, less than about 2 Tesla, less than about 1.5 Tesla, less than about 1 Tesla, less than about 0.5 Tesla, or less than about 0.25 Tesla.

In a related embodiment of the apparatus, the internal magnet comprises at least one component selected from the group: a ferromagnetic compound selected from: iron, iron oxide, neodymium iron boron, nickel, aluminum nickel cobalt, cobalt, and samarium cobalt; a rare earth element selected from scandium, yttrium and a lanthanide. For example, the internal magnet includes neodymium iron boron.

In a related embodiment of the apparatus, the internal magnet has a regular geometrical shape. For example, the regular geometrical shape includes a shape selected from: ellipsoid, cylindrical, ovoid, parallelepiped, slab and tetrahedral.

In a related embodiment of the apparatus, the internal magnet includes a corrosion-resistant coating. For example, the coating includes at least one of chrome and a non-erodible polymer. With a non-erodible polymer coating, the internal magnet in an embodiment of the apparatus is a powder dispersed within the capsule.

In a related embodiment of the apparatus, the drug delivery component is selected from an alginate sphere, a radionuclide, an imaging agent, and a tumor ablative device. For example, the drug delivery component includes at least one alginate sphere.

In a related embodiment of the apparatus, the alginate sphere includes a magnetic microparticle. For example, the magnetic microparticle includes radiopaque iron oxide.

In various embodiments of the apparatus, the anatomic location includes at least one location selected from the gastrointestinal tract including sublingual mucosa, oral cavity, buccal cavity, throat, esophagus, stomach, small and large intestine, and rectum; urogenital tract; and lung and respiratory system.

In various embodiments of the apparatus, the therapeutic agent includes at least one selected from: an anesthetic, an antacid, an antibiotic, a bronchial dilator, a detoxifying agent, a diabetes agent, a diuretic, an enzyme, a hormone, an immunosuppressive agent, a narcotic antagonist, an oxytocic, a radiation source, and a respiratory stimulant.

In a related embodiment of the apparatus, the internal magnet contacts an osmotic pump containing at least one drug release orifice.

In a related embodiment of the apparatus the external magnet is operative on the internal magnet to modulate bias or position of the internal magnet to regulate release of the therapeutic agent.

Another aspect of the invention herein provides a method for formulating a magnetic drug delivery device for a therapeutic agent. The method includes contacting microparticles to alginic acid to produce a microparticle suspension; contacting the therapeutic agent to the microparticles; extruding the microparticle suspension into an aqueous ionic halide salt, thereby producing alginate spheres; and rinsing and freeze-drying the spheres, thereby formulating the magnetic drug delivery device for a therapeutic agent.

In a related embodiment of the method, the suspended microparticles are magnetic. For example, the magnetic microparticles include radiopaque iron oxide. In a related embodiment of the method the alginate includes sodium alginate. In a related embodiment of the method, the ionic halide salt includes a calcium salt. For example, the calcium salt includes calcium chloride ($CaCl_2$). In a related embodiment of the method the alginate spheres include calcium alginate spheres.

In various embodiments of the method the therapeutic agent includes at least one selected from: an anesthetic, an antacid, an antibiotic, a bronchial dilator, a detoxifying agent, a diabetes agent, a diuretic, an enzyme, a hormone, an immunosuppressive agent, a narcotic antagonist, an oxytocic, a radiation source, and a respiratory stimulant.

Another aspect of the invention herein provides a method for treating a subject including administering to an anatomic location of the subject a magnetic pill having: an internal magnet, a drug delivery component and a therapeutic agent; the anatomic location is proximal to a treatment area; applying an external magnet to the anatomic location and monitoring an inter-magnetic attractive force between the internal magnet and the external magnet to adjust the inter-magnetic force in response to an extent of the inter-magnetic force. For example, adjusting includes moving the external magnet.

In an embodiment of the method, adjusting includes manually shifting the external magnet. In an alternative embodiment, adjusting further includes electronically shifting the external magnet. In an alternative embodiment, adjusting further includes removing the external magnet from the vicinity of the internal magnet.

In various embodiments of the method, the subject includes without limitation a human, a dog, a cat, a rat, a mouse, a horse, a sheep, a cow, a primate or other vertebrate species.

In an embodiment of the method, the magnetic pill includes an alginate sphere as the drug delivery component. For example, the alginate sphere includes calcium alginate or sodium alginate.

In various embodiments of the method, the internal magnet includes a magnetic strength of at least about 2 Tesla.

In an embodiment of the method, the internal magnet includes at least one component selected from the group: a ferromagnetic compound selected from: iron, iron oxide, neodymium iron boron, nickel, aluminum nickel cobalt, cobalt, and samarium cobalt; a rare earth element selected from scandium, yttrium and a lanthanide. For example the internal magnet includes neodymium iron boron.

In an embodiment of the method, the internal magnet has a regular geometrical shape. For example, the regular geometrical shape includes a shape selected from: ellipsoid, cylindrical, ovoid, parallelepiped, slab and tetrahedral.

In a related embodiment of the method, the internal magnet includes a corrosion-resistant coating. For example, the coating includes at least one of chrome and a non-erodible polymer.

In various embodiments of the method, the therapeutic agent includes at least one selected from: an anesthetic, an antacid, an antibiotic, a bronchial dilator, a detoxifying agent, a diabetes agent, a diuretic, an enzyme, a hormone, an immunosuppressive agent, a narcotic antagonist, an oxytocic, a radiation source, and a respiratory stimulant.

In an embodiment of the method, the magnetic pill is administered to an anatomic location of the subject. For example, the anatomic location includes at least one location selected from the gastrointestinal tract including sublingual mucosa, oral cavity, buccal cavity, throat, esophagus, stomach, small and large intestine, and rectum; urogenital tract; and lung and respiratory system.

In an embodiment of the method, the internal and external magnets are monitored and adjusted upon monitoring the inter-magnetic force, further increasing or decreasing the residence time of the therapeutic agent in the anatomic region of the subject.

In an embodiment of the method, the magnetic pill has without limitation any suitable convenient shape, for example, is selected from a tablet, a rod, and a capsule, and includes an osmotic pump, an electromechanical drug delivery device, a ferromagnetic permanent magnet, and a combination thereof. The osmotic pump has at least one or a plurality of orifices through which drug is released. For example the administered magnetic pill contains a radionuclide or tumor ablative device.

In various embodiments of the method, the ferromagnetic component includes at least one of iron, iron oxide, neodymium iron boron, nickel, aluminum nickel cobalt, cobalt, samarium cobalt; a rare earth element such as scandium, yttrium and a lanthanide.

An embodiment of the method includes aligning the internal and external magnets.

In an embodiment of the method, the external magnet includes at least one ferromagnetic component selected from the group of: iron, iron oxide, neodymium iron boron, nickel, aluminum nickel cobalt, cobalt, samarium cobalt; a rare earth element such as scandium, yttrium; and a lanthanide.

Another aspect of the invention herein provides a method of using a magnetic drug delivery device to deliver a therapeutic agent to an anatomic location of a subject including orally administering the device to a subject, the device having an internal magnetic dose having an internal magnet, a drug delivery component and the therapeutic agent; applying an external magnet and monitoring an inter-magnetic attractive force and distance between the internal magnetic dose and the external magnet; observing the internal dose motion in real-time using biplanar videofluoroscopy; and, modulating the force exerted on tissue underlying the internal magnet, thereby confirming the anatomic position of the internal magnet and optimizing control of position and force exerted on tissue, thereby delivering the dose to an anatomic location. For example, modulating position of the external magnet is a function of at least one of the inter-magnetic attractive force and distance.

An embodiment of the method includes verifying anatomic position and internal localization by monitoring the inter-magnetic attractive force and distance between the internal and external magnets.

An embodiment of the method includes applying the external magnet and monitoring bioavailability and bioactivity of the therapeutic agent.

In various embodiments of the method, the internal and external magnets include at least one ferromagnetic compound selected from: iron, iron oxide, neodymium iron boron, nickel, aluminum nickel cobalt, cobalt, and samarium cobalt; a rare earth element selected from scandium, yttrium and a lanthanide.

An aspect of the invention herein provides a method of orally administering an agent to a specific region within a human, a dog, a cat, a rat, a mouse, a primate or other species such that the orally administered agent includes a drug delivery device.

An embodiment of the method includes the orally administered agent as a tablet, capsule, osmotic pump, electromechanical drug delivery device, ferromagnetic permanent magnet, and a combination thereof.

An embodiment of the method includes evaluating a potential therapeutic agent effect on an organ or tissue as delivered localized to the organ or tissue. For example, the dose delivered localized is less than a systemic dose.

An embodiment of the method has agent as an imaging agent.

BRIEF DESCRIPTION OF THE DRAWINGS

FIG. 2 panel A is a schematic of a setup for retaining magnetic pills within intestines visualized by biplanar fluoroscopy.

FIG. 2 panels B and C are still photographic images acquired from biplanar fluoroscopic videos showing magnetic model pill retention for 12 hours with the cyclic application of an external magnetic force. Insets show magnified views of the magnetic model pill, having a radiopaque cylindrical NIB magnet with less radiopaque iron-loaded alginate beads on either end, localized in the small intestine.

FIG. 2 panel D is a drawing of an exemplary 3D trajectory plot of a model magnetic pill moving in response to a single force cycle of an external magnet after filtering. Arrows point along the trajectory in the direction of increasing time.

FIG. 2 panel E is a line graph of an exemplary inter-magnetic force plotted as a function of travel along mode 1. Slopes of the best fit lines to the ascending, descending, and whole cycle values of the elasticity coefficient of the internal magnet show the effective elastic constants of the intestinal tissue in response to force cycling. Observed hysteresis in the inter force-travel curve corresponds to the viscoelastic properties of the tissue.

FIG. 2 panel F is a bar graph of tissue elastic constant plotted as a function of time after the start of magnetic retention (N=5) showing that there is no significant change ($P_{asc}=0.52$, $P_{des}=0.68$, $P_{wc}=0.48$) in tissue elasticity during 12 hours of magnetic retention, indicating negligible change in the mechanical integrity of intestinal tissue. Error bars represent standard error of the mean (s.e.m.)

FIG. 3 panel A is a set of photographs showing x-ray confirmation of magnetic pill retention in the small intestines of rats (N=6) demonstrating the efficacy of use of an external magnetic force to obtain magnetic retention. Orally administered magnets are circled in white.

FIG. 3 panel B is a distribution plot of inter-magnetic force as a function of inter-magnetic distance in vitro and in vivo. The plot shows minimal differences thereby enabling the accurate prediction of magnetic pill localization in vitro for use in choosing the appropriate magnet pair for achieving localized drug delivery in any region of the GI in a species.

FIG. 3 panel C is a bar graph showing comparison of median peak inter-magnetic force, net inertial force, and tissue force (N=5). A negligible fraction (0.0005±0.0005%) of inter-magnetic force translated into net inertial force demonstrating that the measured inter-magnetic force was a good approximation of the force imparted by the internal magnet upon the underlying intestinal tissue. Error bars represent s.e.m.

FIG. 5 panel a shows therapeutic-loaded hydrogel spheres and an internal magnet enclosed in a water soluble gelatin capsule. In this panel, A is the external magnet, B is the internal magnet, C is therapeutically-loaded hydrogel spheres and D is the water soluble gelatin capsule.

FIG. 5 panel b shows therapeutic-loaded hydrogel spheres, at least one of which contains nanoparticles, and an internal magnet enclosed in a water soluble gelatin capsule. In this panel, A is the external magnet, B is the internal magnet, C is the therapeutically-loaded hydrogel sphere, D is therapeutically-loaded nanoparticles contained within a hydrogel sphere and E is the water soluble gelatin capsule.

FIG. 5 panel c shows a therapeutic agent, with or without excipients, and an internal magnet with adhesive enclosed in a gelatin capsule that has an insoluble portion, containing the Magnet and the agent, and a soluble portion that caps the contents (encloses the contents). In this panel, A is the external magnet, B is the internal magnet, C is the adhesive, D is the water soluble portion of a gelatin capsule, E is therapeutic with or without excipients and F is the water insoluble portion of the gelatin capsule FIG. 5 panel d shows nanoparticles of therapeutic agent, with or without encapsulating agents or excipients, and an internal magnet with adhesive enclosed in a gelatin capsule that has an insoluble portion containing the magnet and the agent, and a soluble portion that caps the contents [encloses the contents]. In this panel, A is the external magnet, B is the internal magnet, C is the adhesive, D is the water soluble portion of a gelatin capsule, E represents nanoparticles of therapeutic with or without encapsulating agents or other excipients and F is the water insoluble portion of a gelatin capsule.

FIG. 5 panel e shows a therapeutic-permeable, control-release capsule enclosing a therapeutic agent with or without excipients and an internal magnet with adhesive. In this panel, A is the external magnet, B is the internal magnet, C is the adhesive, D is therapeutic permeable release controlling capsule and E is therapeutic with or without excipients.

FIG. 5 panel f shows a therapeutic-permeable, control-release capsule, enclosing a therapeutic agent with or without excipients and an internal magnet with adhesive, and the capsule is surrounded by an environmentally-responsive coating such as a pH-sensitive polymer. In this panel, A is the external magnet, B is the internal magnet, C is the adhesive, D is therapeutic permeable release controlling capsule, E is environmentally responsive coating (e.g. pH sensitive polymer) and F is therapeutic with or without excipients.

FIG. 5 panel g shows a therapeutic-permeable, control-release capsule enclosing nanoparticles of therapeutic agent with or without encapsulating agents or excipients and an internal magnet with adhesive, and the capsule is surrounded by an environmentally-responsive coating such as a pH-sensitive polymer. In this panel, A is the external magnet, B is the internal magnet, C is the adhesive, D is therapeutic permeable release controlling capsule, E is environmentally responsive coating (e.g. pH sensitive polymer), and F is nanoparticles of therapeutic with or without encapsulating agents or other excipients.

FIG. 5 panel h shows a water-insoluble capsule with a therapeutic-releasing orifice covered by an environmentally-responsive coating such as a pH-sensitive polymer, the capsule enclosing a therapeutic agent with or without excipients and an internal magnet with adhesive. In this panel, A is the external magnet, B is the internal magnet, C is the adhesive, D is water-insoluble capsule, E is therapeutic with or without excipients, F is the therapeutic releasing orifice and G is environmentally responsive coating (e.g. pH sensitive polymer).

FIG. 5 panel i shows a water-insoluble capsule with a therapeutic-releasing orifice covered by an environmentally-responsive coating such as a pH-sensitive polymer, the capsule enclosing nanoparticles of therapeutic agent with or without encapsulating agents or excipients and an internal magnet with adhesive. In this panel, A is the external magnet, B is the internal magnet, C is the adhesive, D is water-insoluble capsule, E represents nanoparticles of therapeutic with or without encapsulating agents or other excipients, F is the therapeutic releasing orifice and G is environmentally responsive coating (e.g. pH sensitive polymer)

FIG. 6 panel a shows a magnetic medical device, such as a tumor ablative device, which includes an internal magnet that is enclosed in an ingestible, water-impermeable housing. In this panel, A is an external magnet, B is the internal magnet, C is the medical device, e.g. a tumor ablative device and D is the ingestible water-impermeable housing.

FIG. 6 panel b shows a tablet containing one or more therapeutic agents and an internal magnet. In this panel, A is an external magnet, B is the internal magnet, and C is the tablet containing one or multiple therapeutic (s).

FIG. 6 panel c shows a tablet containing one or more nanoparticle therapeutic agents, which are encapsulated or unencapsulated and an internal magnet. In this panel, A is an external magnet, B is the internal magnet, C is the tablet containing one or multiple nanoparticle encapsulated or unencapsulated therapeutic(s).

FIG. 6 panel d shows a compressed tablet with a partial water-insoluble coating, containing one or more therapeutic agents and an internal magnet. In this panel, A is an external magnet, B is the internal magnet, C is the compressed tablet containing one or multiple therapeutic(s) and D is the water-insoluble partial coating.

FIG. 6 panel e shows a compressed tablet with a partial water-insoluble coating, containing nanoparticles of one or more therapeutic agents, which are encapsulated or unencapsulated and an internal magnet. In this panel, A is an external magnet, B is the internal magnet, C is the compressed tablet containing one or multiple nanoparticle encapsulated or unencapsulated therapeutic(s) and D is water-insoluble partial coating.

FIG. 6 panel f shows a magnetic osmotic pump device with a therapeutic-releasing orifice, containing one or more therapeutic agents and an internal magnet. In this panel, A is an external magnet, B is the internal magnet, C is the osmotic pump containing one or multiple therapeutic(s), D is the therapeutic releasing orifice and E is a water permeable membrane.

FIG. 7 panel A shows a magnetic pill in a closed position, in which an internal magnet is attached to a compressive element such as a spring and containing a therapeutic agent with or without excipients. In this panel, A is the external magnet, B is the internal magnet, C is a compressive element, D is therapeutic with or without excipients, E is water-insoluble capsule and F is therapeutic releasing orifice. The inter-magnetic force between the external and internal magnets is maintained at a low level at which the internal magnet blocks the therapeutic-releasing orifice.

FIG. 7 panel B shows the magnetic pill of panel A in an open position. In this panel, A is the external magnet, B is the internal magnet, C is a compressive element, D is therapeutic with or without excipients, E is water-insoluble capsule and F is therapeutic releasing orifice. The inter-magnetic force is set at a high level at which the internal magnet is compressed, opening the therapeutic-releasing orifice.

DETAILED DESCRIPTION

Figure 1:
FIG. 1 is a photograph of the oral magnetic device, including a cylindrical neodymium iron boron magnet flanked by two iron-loaded alginate spheres and next to a U.S. quarter for size comparison.
Figure 2A:
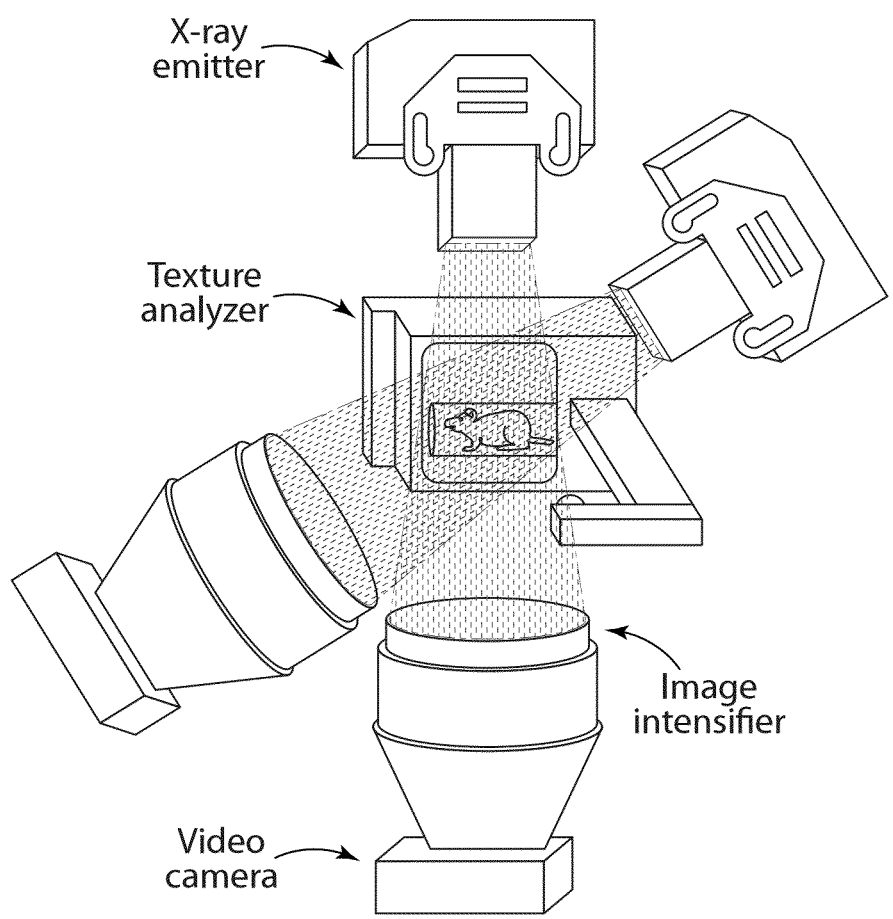
FIG. 2 is a set of drawings, photographs, a line graph and a bar graph showing biplanar videofluoroscopic tracking of magnetically retained model pills in vivo.
Figure 2B:
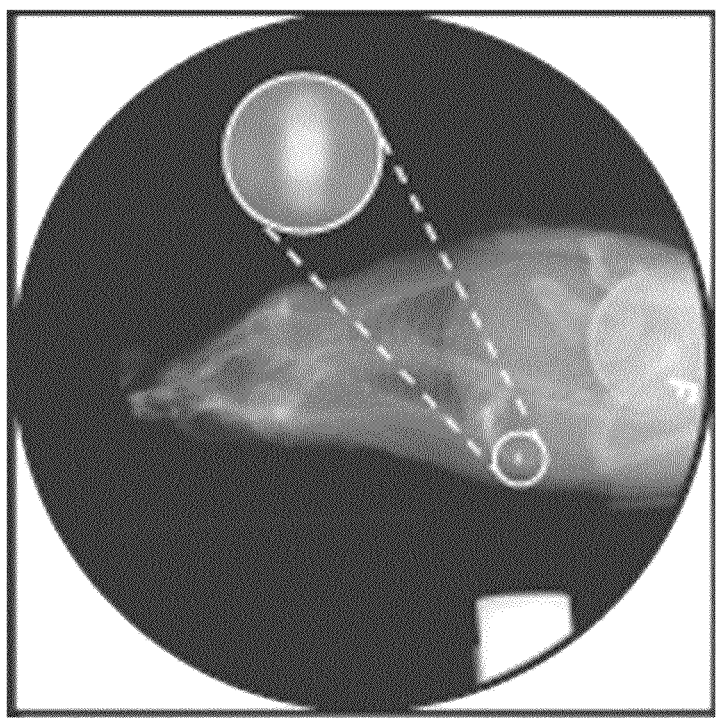
Figure 2C:
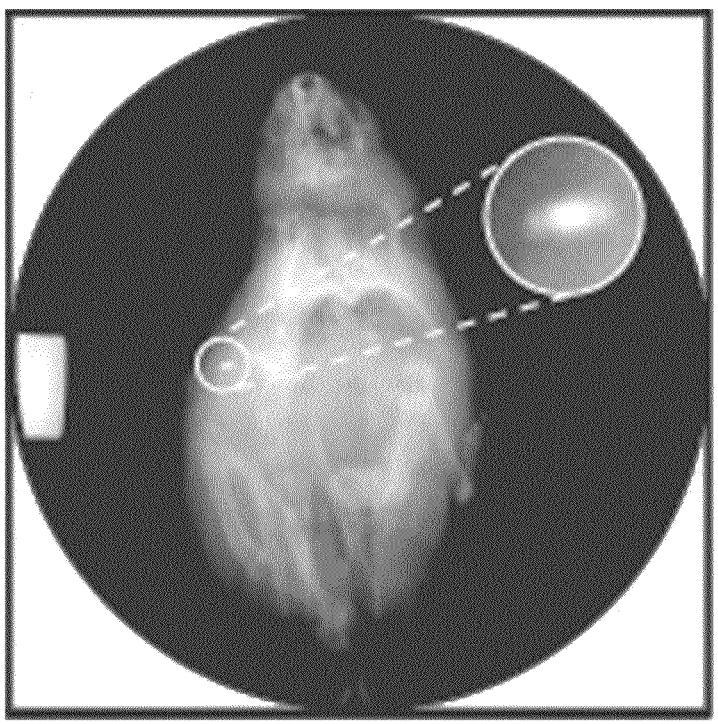
Figure 2D:
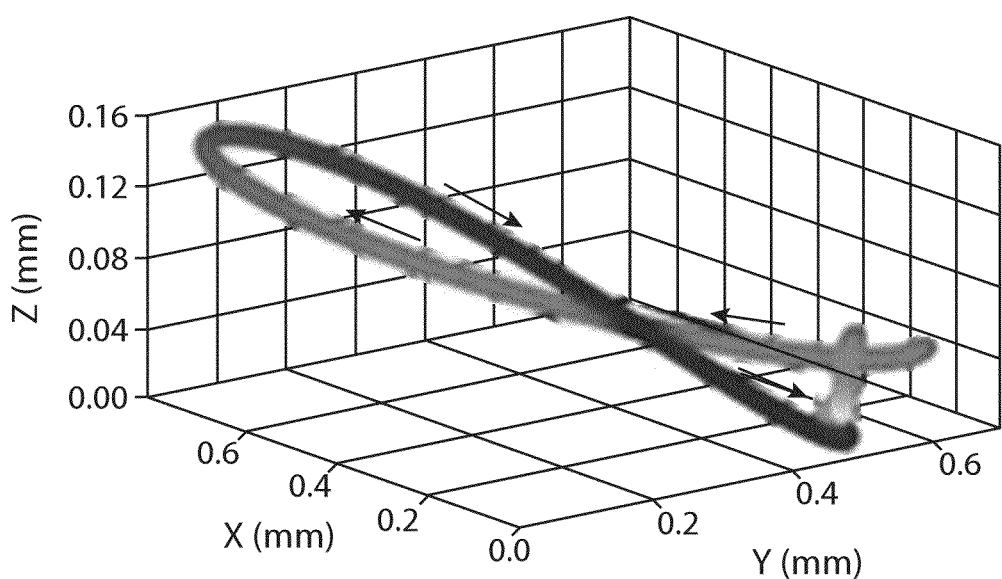
Figure 2E:
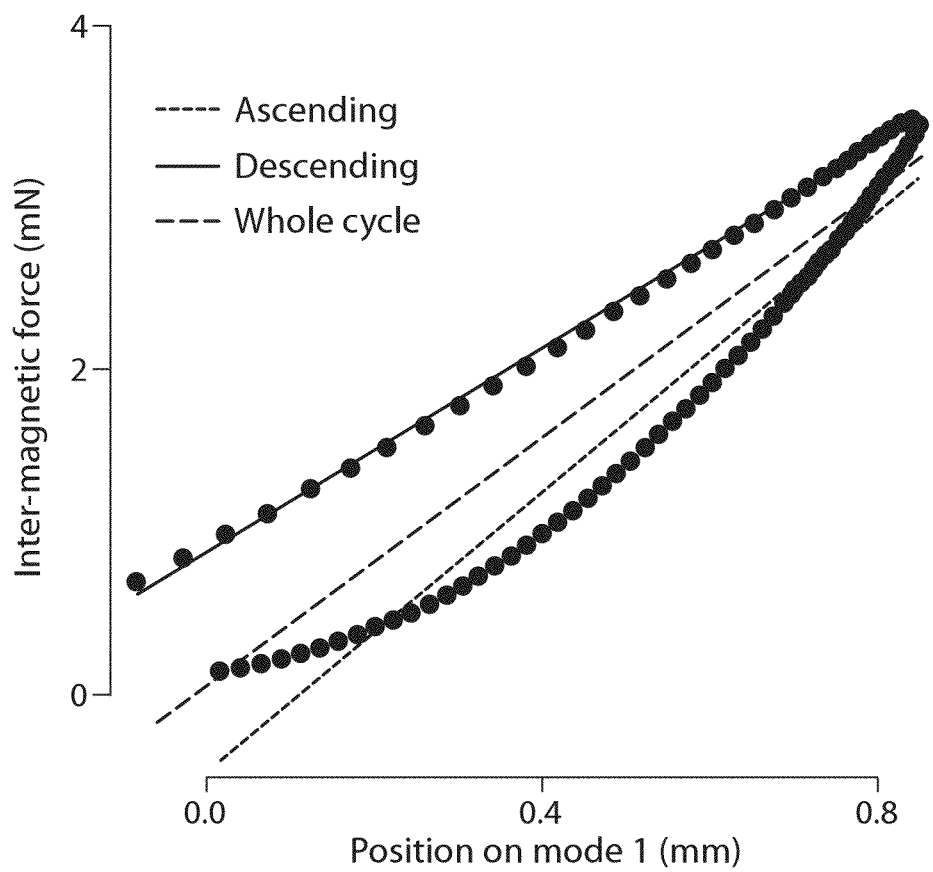
Figure 2F:
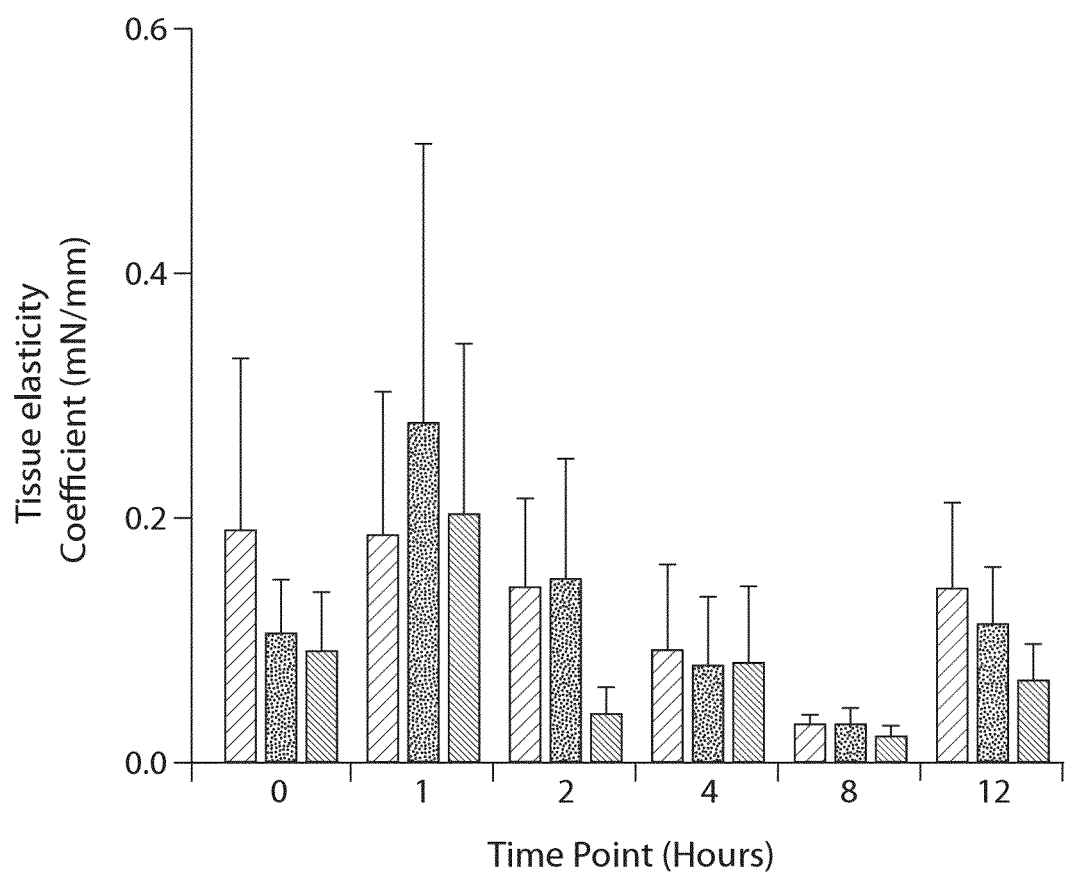

Embodiments of the invention herein provide a magnet-based delivery system visualized by biplanar videofluoroscopy in vivo that yielded real-time monitoring and control over the duration of residence of model magnetic pills in the small intestines of an animal model subject (rats). The system herein retained drugs for up to 12 hours in regions of the GI tract controlled by the force applied by the orally ingested magnet to the intestinal wall. Methods herein relate to retaining the device at a location in the GI tract, which was visually confirmed with respect to the anatomical location of the oral dose. The device was monitored and the inter-magnetic force was controlled to ensured safe capture of the oral dosage in the appropriate region of the GI[1,7].

Data shown in examples herein represent a significant step forward in the ability to safely and effectively localize magnetic pills anywhere within the gastrointestinal (GI) tract. The oral drug delivery system adds to the state of the art the ability to monitor the force exerted by the pill on the tissue and to locate the magnetic pill within the test subject all in real time. This method ensures both safety and efficacy of magnetic localization during the oral administration of any pill-based delivery systems The data obtained from a force-regulated magnetic pill retention system show both monitoring and regulating the force between an external magnet and a magnetic pill. Force monitoring and biplanar fluoroscopy provide real time feedback on the safety and efficacy of magnetic pill retention. Tissue safety is ensured both during the experiments by tissue stiffness monitoring and post hoc by histology. Also, quantitative guidelines are calculated for translating the method to other animal species, including humans along with an in vitro/in vivo correlation for assessing the ability of a given magnetic dosage and an external magnet to achieve GI localization.

In the past, magnetic localization methods required the analysis of a secondary biomarker (e.g. blood measurement, bioavailability) and even in this case it was unclear if the results were a directly correlated with localization of the magnetic delivery system. The magnetic force monitoring herein ensures localization in real time and the anatomic location of the magnetic pill is monitored in three dimensions with great accuracy through the utilization of biplanar videofluoroscopy. Thus the system results in a tool to directly evaluate whether localization confers a therapeutic benefit to the patients.

The magnetic pill localization system for oral drug delivery further provides investigators with the tools for fundamental investigations into site-specific delivery of therapeutics. The methods and system can test therapeutics that have specific windows of GI absorption (e.g. furosemide, metformin, omeprazole, etc) for ability to correct pathophysiologies under conditions in which these agents are localized in the region of highest absorption for an user-determined duration. Additionally, these methods are appropriate for localized delivery to GI pathophysiologies such as colon cancer, irritable bowel syndrome, acid reflux, etc. The expected improvement in therapeutic efficacy may be used preventatively, for example for acid reflux which is epidemiologically predictive for Barrett esophagous and development of esophageal cancer. Outcome of prolonged localization for a therapeutic agent can be directly evaluated with the innovations in both in vitro and in vivo conditions described in examples herein, for treating diseases through the analysis of localized drug delivery.

Examples herein provide a method for monitoring the force applied by an orally administered magnetic dosage to the GI tissue, to ensure safety and efficacy of prolonged retention at a site of therapeutic interest. Localized oral drug delivery that is externally localizable and capable of external monitoring is herein shown to be suitable to deliver therapeutics for inflammatory bowel disease to the colon, and to deliver orally administered chemotherapeutics to GI cancers, and oral vaccines to the ileum[1-12]. Examples herein show benefits of localized administration of therapeutics compared to systemic administration of therapeutics.

The position of an external magnet between upper and lower inter-magnetic force bounds defined by the user was constantly adjusted by a computer-controlled material testing device equipped with a load cell that has a programmed feedback loop. As a result, GI tissue was exposed to the smallest force possible that still retains the magnetic oral dose. Magnetic localization resulted in prolonged intimate contact between the dose and the absorptive GI epithelium. The magnetic localization promoted uptake and bioavailability without damaging intestinal tissue.

External magnets were used in previous examples to improve the bioavailability of orally administered proteins including insulin[4], narrow absorption window (NAW) therapeutics including acyclovir[1,8] and therapeutics for site-specific pathologies including bleomycin for esophageal cancer[9]. In these reports, the magnet was applied in a fixed position, and there was no information regarding monitoring inter-magnetic force or visually verifying the capture of the oral dosage[1,4,8,9]. Early efforts to test GI retentiveness for orally administered magnetic objects showed the maximal attractive force between a dosage and an external magnet, either to retain a large dosage form at the site of interest[8] or to increase the uptake of magnetic nanoparticle formulations[2]. Shapiro described magnetic drug delivery of drugs attached to extremely small magnetic particles that are directed to specific locations near the surface of the body using magnetic fields from stationary magnets outside the body. These are delivered intravenously to the circulatory system, and are localized by the external magnets to a target portion of the body[20]. The small size of the particle results in extravasation to tissues generally and possible intracellular uptake.

Orally administered model doses consists of a cylindrical neodymium iron boron (NIB) magnet ($\Phi$=1.6 mm, length=1.6 mm) coated in chrome and a non-erodible polymer to ensure that the magnet is not damaged within the GI. A freeze dried calcium alginate sphere containing the internal magnet, (radiopaque iron oxide microparticles) was placed at either end of the magnet and held in place by the attractive force of the internal magnet (FIG. 1). Alginate spheres were loaded with therapeutics[13].

Materials suitable for placement within the device include drug delivery devices include those that are well known in the pharmaceutical arts, for example biological delivery vehicles, such as liposomes, microspheres, nanospheres, micelles, vesicles, capsules, needles, or rods, and combinations thereof, however the uses are contemplated to be applicable also to newly developed drug delivery materials. The materials may be made out of a suitable biocompatible material such as chitosan, dextran, poly(lactic acid), starch, poly(vinyl alcohol), polyalkylcyanoacrylate, polyethylene imine, carbon, polysaccharides, heparin, gelatin, viral shells, or proteins. A magnetizable object may be a cell modified to contain or to be attached to a magnetizable material. The objects may have various coatings or attached substances, for example, a layer of carbohydrates may be attached to the objects in order to prevent aggregation (clumping) and a phosphate coating may be used to enhance in vivo residence time.

The magnetic responsiveness of the device is derived from inclusion of at least one ferromagnetic material such as magnetite, iron, nickel, cobalt, dysprosium, gadolinium, gallium, magnesium, yttrium-iron-garnet, neodymium-iron-boron, or samarium-cobalt, or another ferromagnetic material that reacts to a magnetic field such as Heusler alloys and rare earths or lanthanides. Ferromagnetic materials are unique in their ability to retain their own magnetic field, and therefore are useful as materials for construction of permanent magnets. On the other hand, the magnetic properties of paramagnetic or diamagnetic or materials can only be observed and measured when they are placed in an external magnetic field. Materials having "paramagnetic" properties are attracted by a strong magnetic field, whereas those repelled are called, "diamagnetic". A lanthanide is any element from the group consisting of lanthanum, cerium, praseodymium, neodymium, promethium, samarium, europium, gadolinium, terbium, dysprosium, holmium, erbium, thulium, ytterbium, and lutetium.

The magnetically responsive material is preferably biocompatible, and non-biocompatible coated materials with a biocompatible coating or layer, or non-biocompatible are also within the scope of device suitable compounds. A radioactive particle that is meant to result in tissue damage to effect radiotherapy of tumor tissue is suitable for inclusion in the device. The magnetically responsive material forms an integral part of the object, for example a particle core or a nanorod coating, or is attached to the object, for example attached to the surface. Some magnetizable objects comprise magnetite ($Fe_3O_4$), which has a magnetic susceptibility of about 20 and is five to seven orders of magnitude higher than the magnetic susceptibility of the body. Another magnetizable object has a core of magnetizable material such as iron oxide coated with carbohydrates linked to a therapeutic agent, for example epirubicin, mitoxantrone, or paclitaxel. Still other magnetizable objects comprise a magnetically responsive core coated with a biocompatible material, which protects the magnetic material from the surrounding environment and facilitates functionalization by allowing the attachment of carboxyl groups, biotin, avidin, and other functional groups that act as attachment points for therapeutic agents or targeting molecules.

Devices provided herein are associated with a therapeutic agent (e.g., the therapeutic agent is entangled, embedded, incorporated, encapsulated, bound to the surface, or otherwise associated with the particle). The associated therapeutic agent is for example a drug such as a pure drug (e.g., drugs processed by crystallization or supercritical fluids), an encapsulated drug (e.g., polymers), a surface associated drug (e.g., drugs that are adsorbed or bound to the object surface), or a complexed drug (e.g., drugs that are associated with the material used to foam the object). In other embodiments, the devices are associated with a fluorescent agent or a measurable signal when exposed to light or another external stimulus, which is useful for diagnostics, imaging and sensing.

The term "agent", as used herein means a compound specifically administered to induce a therapeutic effect, and includes compounds having utility for therapeutic and/or diagnostic and/or prophylactic purposes (e.g., therapeutic, diagnostic or prophylactic agents). Therapeutic agents include, without limitations antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), vascular endothelial growth factor (VEGF) inhibitors or antagonists or intraceptors, receptor antagonists, RNA aptamers, antibodies, hydroxamic acids and macrocyclic anti-succinate hydroxamate derivatives, nucleic acids, plasmids, siRNAs, vaccines, DNA binding compounds, hormones, vitamins, proteins, peptides, polypeptides and peptide-like therapeutic agents. Diagnostic agents include, without limitation, dyes, contrast agents, fluorescent agents, radioisotopes (e.g., $^{32}$P, $^{99}$Tc, $^{18}$F, $^{131}$I) and the like that are useful in the diagnosis of diseases, conditions, syndromes or symptoms thereof. A therapeutic agent administered in advance of the detection of a disease, condition, syndrome or symptom is a prophylactic agent.

Other diseases and disorders benefit from therapeutic application of the methods and devices herein. A benefit of localized drug delivery results in increased bioavailability of treatments. Diseases and disorders suitable for treatment include diabetes, for example with metformin; treatment of epileptic seizures, postherpetic neuralgia and peripheral neuropathy, for example with gabapentin; treatment of Parkinson's disease, for example with levodopa; treatment of Lou Gehrig's disease, for example with baclofen; treatment of bacterial infections, for example with ciprofloxacin; treatment of high blood pressure and hypertension, for example with captopril; treatment of congestive heart failure and other edematous conditions, for example with furosemide; treatment of herpes simplex virus, shingles, and HIV, for example with acyclovir; and treatment of osteoporosis, for example with bisphosphonate.

Pharmaceutical Compositions

In an aspect of the present invention, pharmaceutical compositions are described that are embedded in a magnetic device, and the device with the composition optionally includes a pharmaceutically acceptable carrier. In general, the device includes one or more therapeutic agents. The therapeutic agent or agents are selected without limitation from therapeutic agents such as anti-neoplastics, antibiotics, antivirals, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), and hyaluronic acid. However the device and methods herein are useful also with any therapeutic agent, including those not yet described, and are not limited to known agents.

As used herein, the term "pharmaceutically acceptable carrier" means any material included for improving pharmacological properties of the agent, which includes solvents, diluents, or other liquid vehicle, dispersion or suspension aids, surface active agents, isotonic agents, thickening or emulsifying agents, preservatives, solid binders, lubricants and the like, as suited to the particular dosage form desired which are well known in the pharmaceutical arts. *Remington's Pharmaceutical Sciences* Ed. by Gennaro, Mack Publishing, Easton, Pa., 1995 (the contents of which are hereby incorporated by reference), discloses various carriers used in formulating pharmaceutical compositions and techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

The use of devices herein is promoted by contacting the device with a pharmaceutical composition to a target tissue or organ, as described herein. Thus, the invention provides methods for the treatment of the target tissue or organ comprising administering a therapeutically effective amount of a pharmaceutical composition comprising active agents to a subject in need thereof, in such amounts and for such time as is necessary to achieve the desired result. It will be appreciated that this encompasses administering the pharmaceutical agent as a therapeutic measure to promote the delivery of the agent or as a prophylactic measure. In certain embodiments of the present invention a "therapeutically effective amount" of the pharmaceutical composition is that amount effective for promoting the effective agent to the target, for example, sufficient anti-neoplastic agent to reduce size and metastasis of a tumor, or sufficient antibiotic to inhibit growth and viability of bacteria. The compositions, according to the method of the present invention, may be administered using an amount and a route of administration effective for delivery to the target tissue. Thus, the expression "amount effective", as used herein, refers to a sufficient amount of composition to remediate the disease condition at the target location. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, such as size and location of a tumor or infected tissue; age, weight and gender of the patient; diet, time and frequency of administration, drug combinations, reaction sensitivities, and tolerance/response to therapy.

The active agents of the invention are preferably formulated in a slow release dosage unit form for ease of administration and uniformity of dosage. The expression "dosage unit form" as used herein refers to a physically discrete unit of active agent appropriate for the patient to be treated. It will be understood, however, that the total usage of the compositions carried by the device herein will be decided by the attending physician within the scope of sound medical judgment. For the active agent, therapeutically effective dosage can be estimated initially either in cell culture assays or in animal models, usually mice, rats, rabbits, dogs, or pigs. The animal model is also used to achieve a desirable concentration range and route of administration. Such information can then be used to determine useful doses and routes for administration in humans. A therapeutically effective dose refers to that amount of active agent which ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use.

Administration of Pharmaceutical Compositions

After formulation with an appropriate pharmaceutically acceptable carrier in a desired dosage, the pharmaceutical compositions of this invention are administered to subjects, generally humans and other mammals, orally to access the GI tract. Devices herein are also administered rectally, parenterally by surgical implantation, intracisternally, intravaginally, intraperitoneally, bucally, occularly, or nasally, depending on the severity and location of the tumor or infection being treated.

Compositions for rectal or vaginal administration are preferably foimulated with suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the device for immobilization by the external magnet.

Solid dosage forms for inclusion in the device included the active agent mixed with at least one inert, pharmaceutically acceptable excipient or carrier such as sodium citrate or dicalcium phosphate and/or: fillers or extenders such as starches, lactose, sucrose, glucose, mannitol, and silicic acid; binders such as, for example, carboxymethylcellulose, alginates, gelatin, polyvinylpyrrolidinone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, cetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings; release controlling coatings and other coatings well known in the pharmaceutical formulating art. In such solid dosage forms the active agent(s) may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, for example, in a delayed manner. Examples of embedding compositions which can be used include polymeric substances and waxes.

Uses of the Devices

As discussed herein and described in greater detail in the Examples, the devices are useful for delivery and localization of medicaments. In general, it is believed that these devices will be clinically useful in diagnosing and treating disorders of the gastrointestinal tract; the lung epithelium; and the inner surface of kidney tubules; of blood vessels, of the uterus, of the vagina, of the urethra, or of the respiratory tract. The present invention encompasses the treatment of a variety of disorders of the GI tract and other internal epithelial targets including but not limited to, ulcers, tumors, microbial infections, lesions, abrasions, erosions and non-healing wounds. These disorders may be in normal individuals or those subject to conditions such as diabetes, dystrophies, uremia, malnutrition, vitamin deficiencies, obesity, infection, immunosuppression and complications associated with systemic treatment with steroids, radiation therapy, non-steroidal anti-inflammatory drugs (NSAID), anti-neoplastic drugs and antimetabolites.

Delivery using devices herein could also be used to treat gastrointestinal ulcers and help heal the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, devices herein could be used to deliver medicaments to promote the resurfacing of the mucosal surface to aid more rapid healing and to prevent or attenuate progression of inflammatory bowel disease, be used prophylactically or therapeutically to prevent or attenuate mucositis, esophagitis, or gastritis (e.g., to heal lesions associated with oral, esophageal, intestinal, colonic, rectal, and anal ulcers).

Devices could be used to promote urothelial healing. Tissue layers comprising urothelial cells may be damaged by numerous mechanisms including catheterization, surgery, or bacterial infection (e.g., infection by an agent which causes a sexually transmitted disease, such as gonorrhea). The present invention also encompasses methods and devices for treatment and/or diagnosis in the female urogenital tract comprising the administration of an effective amount a medicament associated with the device. Tissue damage in the female genital tract may be caused by a wide variety of conditions including Candida infections, trichomoniasis, Gardnerella, gonorrhea, chlamydia, mycoplasma infections and other sexually transmitted diseases.

Devices could be administered prophylactically to reduce or prevent damage to the lungs caused by various pathological states, for example, to promote the repair of alveoli and bronchiolar epithelium to prevent, attenuate, or treat acute or chronic lung damage. Emphysema, which results in the progressive loss of alveoli, and inhalation injuries (i.e., resulting from smoke inhalation and burns) that cause necrosis of the bronchiolar epithelium and alveoli, could be effectively treated using devices herein to deliver agents to remediate tissue by providing chemotherapy, radiation treatment, lung cancer, asthma, black lung and other lung damaging conditions.

Additional embodiments and examples of the invention are found in the examples and claims below, which are illustrative and are not to be construed as further limiting. The contents of all literature cited herein are hereby incorporated in their entirety by reference.

A portion of these examples is found in a publication entitled: "Localization of Magnetic Pills" by Bryan Laulicht, Nicholas J. Gidmark, Anubhav Tripathi, and Edith Mathiowitz; Proceedings of the National Academy of Sciences, Feb. 8, 2011, vol. 8, no. 6, pages 2252-2257, which is hereby incorporated herein by reference its entirety.

EXAMPLES

Example 1

Magnetic Pill Preparation

Orally administered doses consisted of two freeze dried alginate spheres on either side of a NIB magnet ($\Phi$=1.6 mm, length=1.6 mm, KJ Magnetics, Jamison, Pa.). The alginate spheres were prepared by introducing 30 w/v % iron microparticles (Sigma-Aldrich, Saint Lois, Mo.) suspended in an aqueous 2 w/v % low viscosity sodium alginate (Sigma-Aldrich, Saint Lois, Mo.) into an aqueous 1 w/v % calcium chloride (Sigma-Aldrich, Saint Lois, Mo.) receiving bath. The sodium alginate solution was extruded through a 21 gauge syringe needle at 3 ml/min by a vertically oriented syringe pump (Harvard Apparatus, Holliston, Mass.). Upon entering the receiving bath, the divalent cationic calcium was ionically cross-linked to polyanionic alginate as described previously.[13] Alginate spheres were collected, rinsed with distilled water and then freeze dried overnight. The assembled doses were loaded into size 9 gelatin capsules (Torpac, Fairfield, N.J.) for oral gavage. Magnetic alginate spheres were used to deliver therapeutics in a controlled fashion. The alginate spheres include the dosage form of sufficiently small size for gastric emptying, and having sufficient inter-magnetic strength for retention, which can be readily adapted by scale-up or scale-down for other species of subjects.

Example 2

Force Monitoring of Magnetic Localization

A texture analyzer XT-plus (Texture Technologies, Scarsdale, N.Y.) was modified to hold a subject in an acrylic restraint tube on its base while the load cell containing arm was oriented to move horizontally. The texture analyzer was programmed using Texture Exponent Software (Texture Technologies, Scarsdale, N.Y.) to begin its cycle 50 mm from the outer surface of the acrylic restraint tube and to approach the tube at 0.5 mm/s until a force of 4 mN is reached. Upon reaching an inter-magnetic tensile force of 4 mN, the arm moved away from the subject at constant speed until a minimal force of 1 mN is reached. The cycle, which takes approximately 30 seconds, was repeated for a user-defined period. Force cycling resulted in the intermittent release of retaining force to ensure minimal tissue damage. Real time inter-magnetic force monitoring was used to determine that the internal magnet did not apply undue stress to the GI tissue.

Example 3

Biplanar Videofluoroscopic Spatial Calibration, Visualization, Tracking, and Analysis of Magnet Motion C-arm fluoroscopes (OEC Model 9400) were retrofitted with 30 cm Image Intensifiers (Dunlee model TH9432HX, Dunlee Inc., Aurora, Ill.) and Photron video cameras (Fastcam 1024 PCI, Photron, inc., San Diego, Calif.). Algorithms were executed in MATLAB (The Mathworks, Natick, Mass.) using custom software and a 64-point calibration cube to account for distortion introduced by the fluoroscopes and to determine their 3D positions[14]. MATLAB scripts were embedded in XrayProject version 2.0.7, available for download at http://www.xromm.org. Marker tracking scripts, embedded within XrayProject version 2.0.7 were used to calculate 3D positions of the internal magnet and the external arm[14,15]. A 30 Hz low-pass filter was used to remove breathing artifact in the 3D coordinates of the internal magnet.

Motion of the internal magnet was observed primarily along a single line (the line of motion of the TA aim). Movement in world space was tracked and this line of motion of the TA arm was not precisely contained within either the x, y or z dimension of the calibration cube. Proper Orthogonal Decomposition (POD) was observed to reduce this dimensionality. Mathematically, this technique is identical to Principal Components Analysis (PCA) or Singular Value Decomposition (SVD), transforming 3D coordinate space such that one axis (herein termed mode 1) explains the greatest possible amount of variation in the data[16]. Given three parameters (x, y, and z coordinates, in cube space, over time), the dataset has three modes. Mode 1 explained 98.2±1.8% of variation in position over time, so the position along mode 1 was used as an approximation of movement of the internal magnet. Similar analyses were performed on the position of the TA arm, for which mode 1 explained 98.6±1.3% of the variation.

Force recordings from the Texture Analyzer were synchronized with recordings from the videofluoroscopy by comparing the TA arm position (as measured by the Texture Analyzer) with the position of the arm along mode 1 (according to the dimensionally-reduced videofluoroscope analysis). A MATLAB cross-correlation algorithm was used and correlated timing of these two waves and the TA and fluoroscopy data sets were synchronized.

Example 4

X-ray Verification of Magnetic Localization

Six 600-800 g, male, albino sprague-dawley subjects were used to analyze localization of model magnetic pills for a period of 12 hours. Subjects had access to food and water ad libitum within their acrylic restraint tubes and were handled in accordance with NIH and IACUC guidelines. X-rays were taken prior to the start of and after 12 hours of magnetic localization to test the efficacy of magnetic capture. The six subjects showed successful magnetic intestinal retention each for a period of 12 hours.

Example 5 in vitro Magnetic Force Testing

Figure 3A:
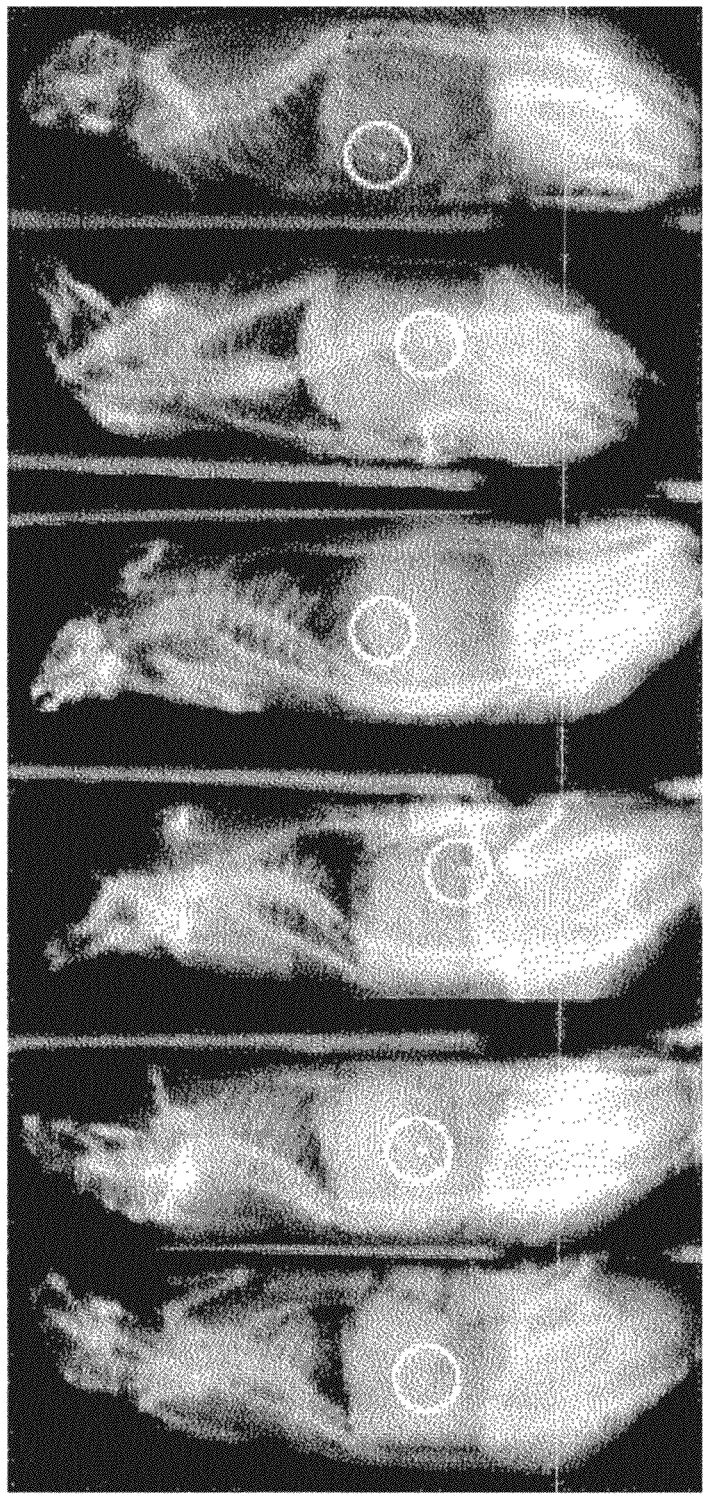
FIG. 3 is a set of photographs, a distribution plot, and a bar graph showing confirmation of magnetic capture by x-ray, of in vitro and in vivo force measurement, and of the force exerted by the internal magnet on underlying tissue.
Figure 3B:
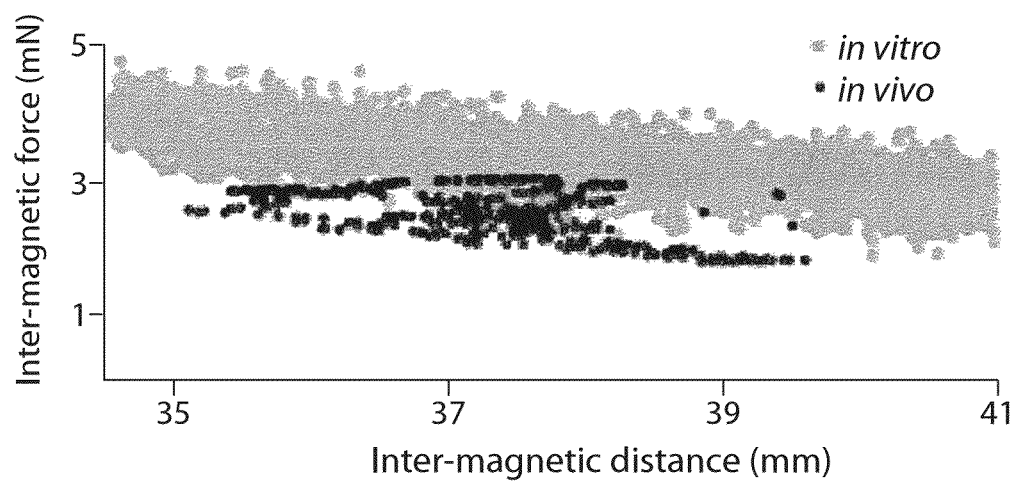
Figure 3C:
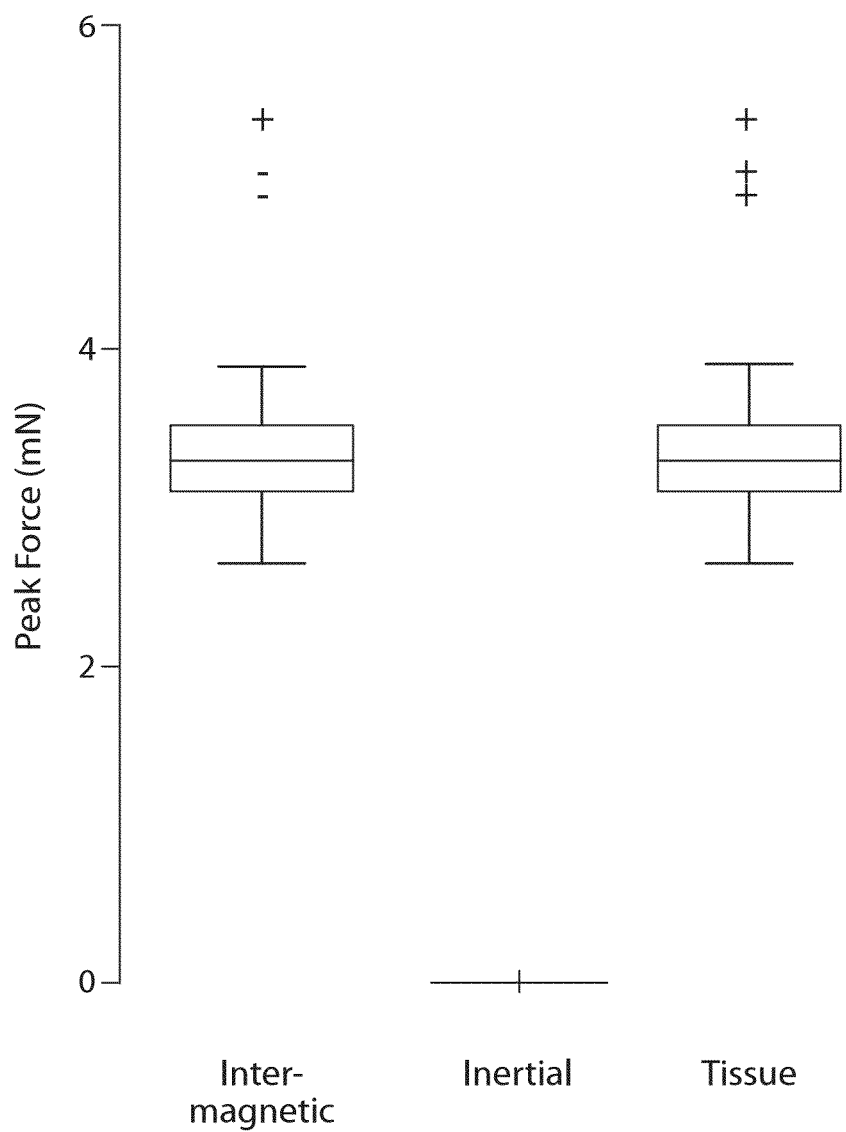

A cylindrical NIB magnet identical to the orally dosed magnets was affixed by cyanoacrylate glue to a non-magnetic aluminum pedestal ($\Phi$=1.6 mm, length=1.6 mm, KJ Magnetics, Jamison, Pa.). The cylindrical external NIB magnet ($\Phi$=25 mm, length=25 mm, KJ Magnetics, Jamison, Pa.) was then brought towards the immobilized magnet and inter-magnetic force and separation distance were monitored. The in vitro force as a function of distance curve was compared to data obtained from the in vivo experiments, in which the inter-magnetic distance was calculated from tracking the location of the internal and external magnets from biplanar fluoroscopic videos. Inter-magnetic force as a function of distance was found to be negligibly different between the in vitro and in vivo cases (FIG. 3 panel B). Therefore in vitro inter-magnetic force as a function of magnet separation testing was used to predict retention of an internal magnet paired with an external magnet. The internal magnet is orally administered as a magnetic pill appropriate in size and magnetic strength for the dimensions of the subject and an estimate of the local, propulsive GI forces experienced during digestion.

Example 6

Administration of the Oral Magnetic Pill

Each dose of the magnetic pill was administered by oral gavage to each subject prior to physical restraint. After the magnetic pill entered the small intestines, the restrained subject was placed on a modified materials testing device without anesthesia (FIG. 2 panel A). A cylindrical NIB magnet ($\Phi$=25 mm, length=25 mm) was brought towards the subject until a maximal force of 4 mN was achieved. The external magnet was retracted from the subject upon reaching the maximum desired force and until a minimal force of 1 mN is reached. The cycle of approach and retraction was repeated with the external magnet moving at 0.5 mm/s for 12 hours. Tissue was observed to have recovered from resulting intestinal vasculature compression and mesenteric stretching between periods of maximal inter-magnetic force using force cycling, i.e., periodically releasing the inter-magnetic force approximately every 10 seconds. Biplanar fluoroscopic videos were recorded at prescribed time points (first instance of retention, and 1, 2, 4, 8 and 12 hours thereafter) to quantify internal dose motion. FIG. 2 panels B and C show exemplary x-ray images from fluoroscopy videos of the magnetic dosage in the small intestines, with co-administration of aqueous barium sulfate for contrast.

Figure 4:
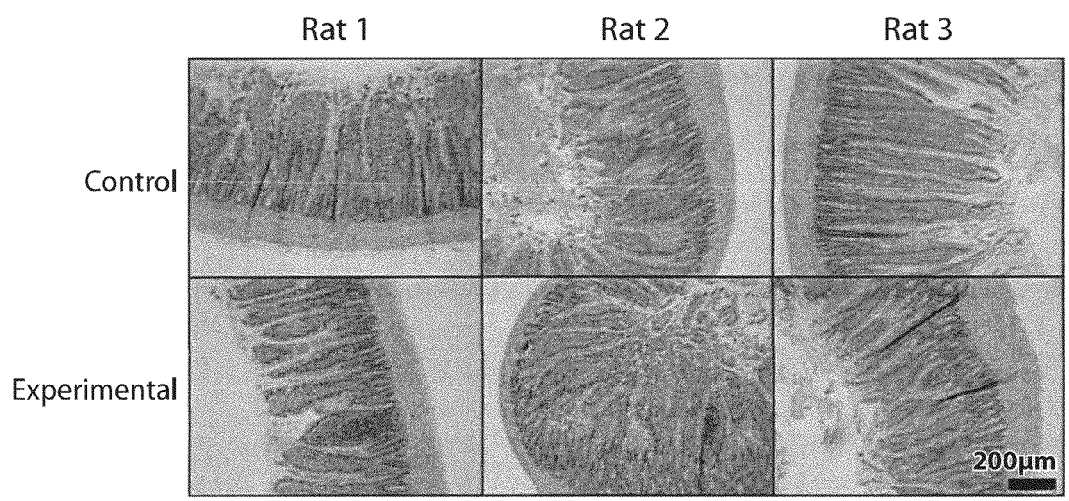
FIG. 4 is a set of bright field micrographs showing hemotoxylin and eosin stained segments of the small intestines in the region of the 12 hour magnetic localization and a distal region where no magnetic localization occurred as a control. All images were acquired at 100× magnification. There is no observable difference among the intestinal sections demonstrating that magnetic retention did not cause inflammation or necrosis.
Figure 5D:
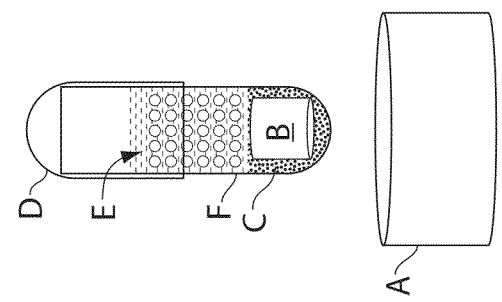
FIG. 5 is a set of drawings of ingestible magnetic pills containing therapeutic agents enclosed in capsules having various solubility and permeability characteristics, and environmentally-responsive coatings. Each drawing shows an external magnet illustrated below the pill.
Figure 5C:
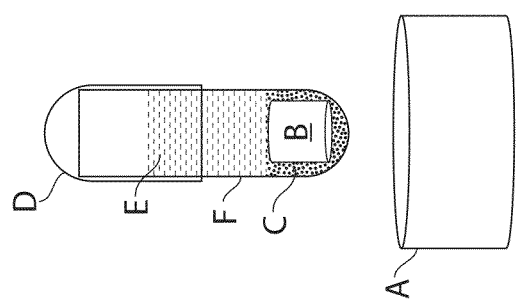
Figure 5B:
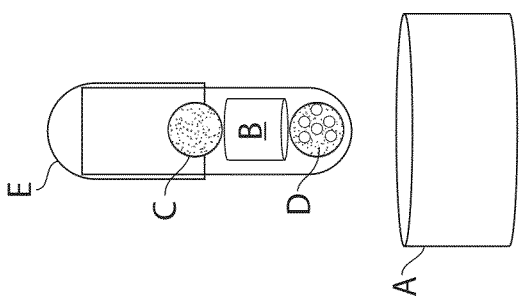
Figure 5A:
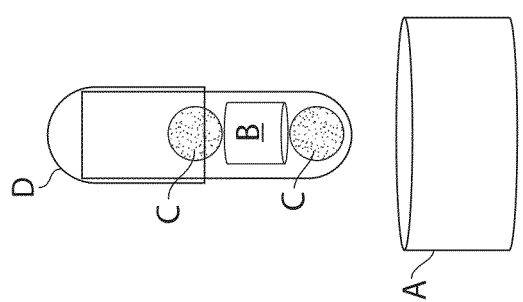
Figure 5I:
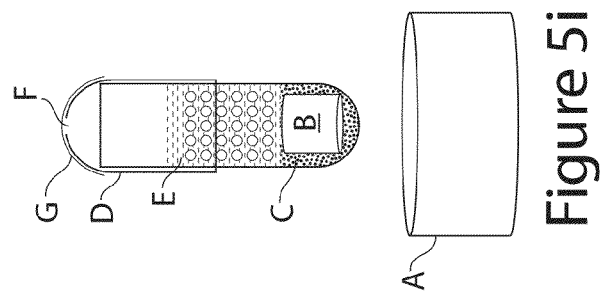
Figure 5H:
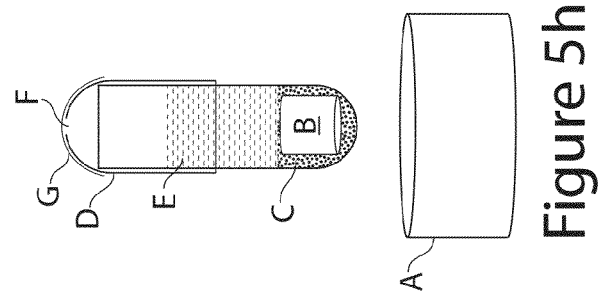
Figure 5G:
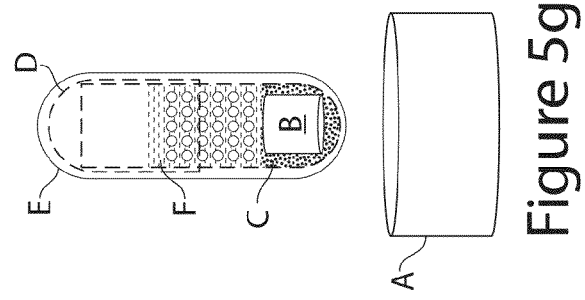
Figure 5F:
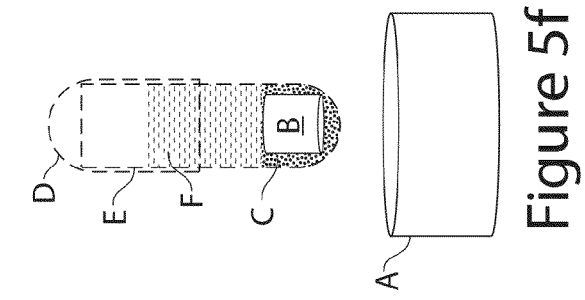
Figure 5E:
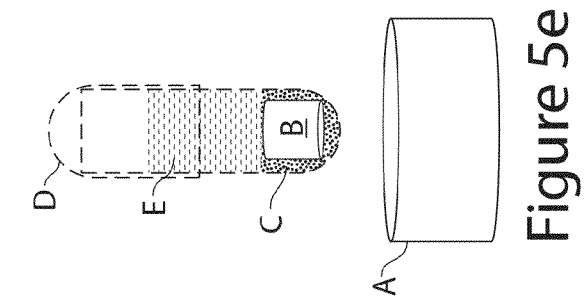
Figure 6C:
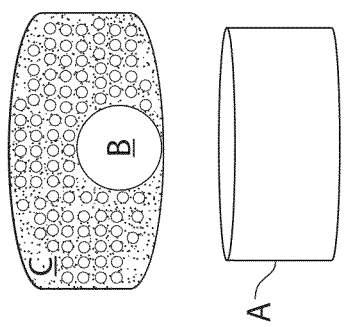
FIG. 6 is a set of drawings of a magnetic medical device, magnetic tablets containing therapeutic agents and an osmotic pump device containing one or more therapeutic agents. Each drawing shows an external magnet illustrated below the device or tablet. The devices are in the form of the ingestible tablets.
Figure 6B:
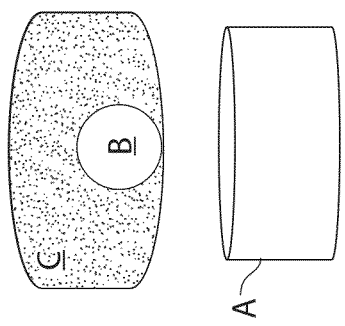
Figure 6A:
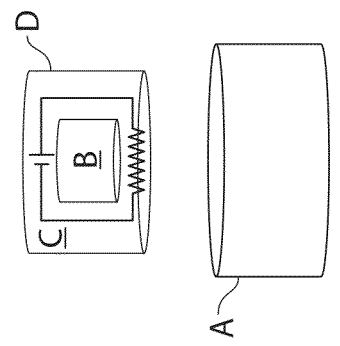
Figure 6D:
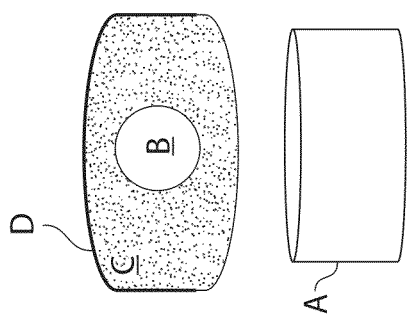
Figure 6E:
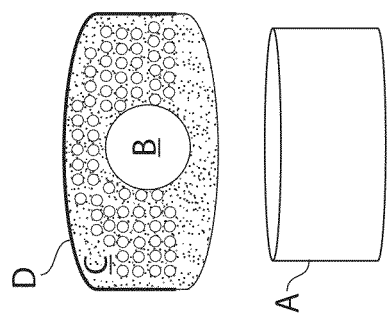
Figure 6F:
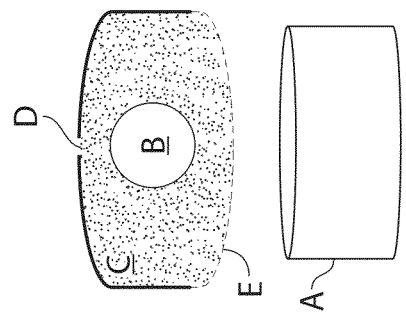

Biplanar x-ray videofluoroscopy was used to visualize the anatomical location and magnet-induced motion of the internal magnet.[14] Three-dimensional position of the internal magnet was tracked over time using orthogonal biplanar fluoroscope videos.[15] Motion of the internal magnet was plotted in three-dimensions during the course of an exemplary force cycle (FIG. 2 panel D). Proper orthogonal decomposition showed that 98.2±1.8% of the three dimensional motion of the pill was described by a single axis (N=5), termed mode 1.[16] Hookean elasticity of tissue calculations were made by taking the slope of the inter-magnetic force as a function of position along mode 1 (FIG. 2 panel E). Due to hysteresis in the force-distance curve associated with the viscoelastic nature of the intestinal tissue, the slope of the ascending, descending, and whole force cycle was measured as a function of time to determine if the tissue retained its mechanical integrity (FIG. 2 panel F). The elastic constants measured at the start of the retention were not significantly different from those measured at later time points as shown by one-way analysis of variance (P=0.52, P=0.68, and P=0.48 with respect to the ascending, descending, and whole force cycle respectively). Therefore, the intestinal tissue maintained its mechanical integrity throughout 12 hours of retention (N=5). A post-mortem histological review confirmed no signs of damage caused by retention (FIG. 4). Magnets, such as neodymium iron boron permanent magnets used in this example, with a field strength of less than 2T, are classified by the FDA as insignificant risk devices.

Example 7

Histology

Intestinal tissue samples from 3 rats were recovered post mortem in the region of magnetic retention and 2 cm distal to the region of magnetic retention (FIG. 4). Sections were fixed in paraformaldehyde, embedded in paraffin, sectioned, and stained with hemotoxylin and eosin. Sections were imaged on a Zeiss Axiovert 200M (Oberkochen, Germany) motorized inverted microscope equipped with an AxioCam MRc5 color camera (Zeiss, Oberkochen, Germany). Intestinal tissue at the site of localization showed no difference in mechanical integrity or signs of inflammation from distal control samples indicating that the method of magnetic retention did not have immediate negative effects on the intestinal tissue under the testing conditions.

Example 8

Efficacy and Reproducibility Test of Magnetic Localization

Standard x-ray was used in six additional subjects to confirm effectiveness and reproducibility of real-time force monitoring magnetic localization for 12 hours (FIG. 3 panel A). It was observed in each subject that the magnet remained within the small intestines for 12 hours. None of the subjects had dosages within the small intestines after 12 hours without an external magnet present. Inter-magnetic force measurements dropped when the entire rat was removed from the materials testing device indicating the loss of magnetic retention. Due to the slow mean velocity of pill intestinal transit (2 cm/min in the rat jejunum) and the length of the rat jejunum (~400 cm), it would be possible to remove the external magnet, up to about 1 hour before the dose has progressed into the next segment of the GI[17].

Inter-magnetic force as a function of inter-magnetic distance was observed to be only minimally affected by the presence of a live subject (FIG. 3 panel B), which demonstrates that magnet size and strength selection in vitro translate well into in vivo examples in a subject species. Capture efficacy is evaluated in vitro prior to live subject studies using readily quantifiable parameters including the lateral dimensions of the experimental subject, the inter-magnetic force, and the GI propulsive force in the region of retention. If the inter-magnetic force measured at the physiologically relevant distance between the nearest external surface of the subject and the internal magnet is greater than the maximal propulsive force in the region, estimated by analyzing the inertial force from high resolution magnetic pill tracking data[18], magnetic capture is useful for an animal species including humans.

To quantify the net inertial force experienced by the internal magnet, the three-dimensional position of the internal magnet was tracked as a function of time and its instantaneous acceleration (FIG. 3 panel C)[18]. Inter-magnetic force was observed to closely approximate the force the magnet applies to the GI tissue since the inertial net force was only 0.0005±0.0005% of the measured inter-magnetic force. Normalizing the force experienced by the tissue by the cross-sectional area of contact with the internal magnet yielded a measure of the stress experienced by the tissue which was observed in a range of 4 mm to 15 mmHg. Manometric jejunal pressures recorded in rats range from 4-16 mmHg indicating that that retention stresses observed were within the normal physiological range for rat jejunal tissue[19].

Example 9

Manufacture Designs of Various Magnetic Pills for General Applications

Diseases and disorders here treated more efficiently as a therapeutic agent in an ingestible magnetic pill is released in concentrated form at an anatomic location of a target tissue or organ in need of the treatment, rather than being diluted by systemic administration into the entire subject, with concomitant loss by excretion and metabolism. Further, agent bioavailability is directed to the immediate vicinity of the target and the resulting treatment is concentrated to the particular anatomic location. The pill is manufactured to have a size and shape appropriate to be ingested or implanted in a minimally invasive procedure.

Therapeutic agents are contained within the pill and diffuse or are released from the pill locally to the anatomic location. The pill in various embodiments herein is manufactured to have controlled release characteristics, which regulate the rate and the site of release by arranging particular properties of salvation or dispersal of a tablet or solubility properties of a capsule or a portion of a capsule, thereby controlling an amount of the agent and limiting bioactivity to the treatment site. In alternative embodiments the capsules have a specific set of characteristics, e.g., extent of solubility and permeability characteristics; inclusion of the therapeutic agent incorporated into nanoparticles or microparticles to increase bioavailability and bioactivity at the treatment site; and, design of the coating of the tablet or outer capsule for enclosing the internal magent and the therapeutic agent.

The terms "nanoparticle" and "microparticle", as used herein, refer to a formulation of a therapeutic agent which which the agent is delivered to a subject in a form having a reduced size resulting in a larger surface-to-volume ratio compared to macroscaled agents. The reduced-size particles demonstrate greater bioactivity and thus increase efficacy of the treatment in an anatomic location compared to larger sized formulations of the same agent. A nanoparticle ranges from about 100 nm to about 250 nm in diameter, for example, from about 1 nm to about 100 nm, from about 1 nm to about 250 nm in diameter, from about 100 nm to about 500 mm, or to about 750 nm or about 1000 nm. A microparticle ranges in size from about 100 µm to about 250 µm in diameter, for example, from about 1 µm to about 100 µm, from about 1 µm to about 250 µm in diameter, from about 100 µm to about 500 µm, or about 750 µm or about 1000 µm.

The structure of the magnetic pill includes in various embodiments herein a tablet or a capsule, for example, a conventional capsule which has two overlapping components: an inner hollow component to contain during loading of the capsule the therapeutic agent for example formulated as nanoparticles or microparticles, and an outer hollow cap having an inner diameter larger than the outer diameter of the inner component of the capsule, such that the cap component acts as a lid or cover and extends of the inner component.

The magnetic pill includes in an embodiment a water-soluble capsule and an internal magnet and at least one therapeutic agent, for example, a plurality of magnetic hydrogel spheres loaded with the therapeutic agent (FIG. 5 panel a). The water-soluble capsule forms a container that contains the internal magnet and therapeutic agent and maintains the proximity of these components. Spheres composed of a hydrogel are water-insoluble, the hydrogel including a highly absorbent polymer for example, alginate, that in the dissolved condition contains for example about 95% of a liquid component, generally water, for example at least about 70% water, at least about 80% water, or at least about 90% water. The hydrogel spheres in an embodiment herein are formulated to contain magnetic microparticles and at least one therapeutic agent. The agent is released from the hydrogel, for example, in response to an environmental change, for example an increase or decrease in pH, and the magnetic microparticles are maintained with the pill.

The magnetic pill is manufactured in an embodiment herein to dissolve upon ingesting, for example, a capsule having an outer gelatin coating. The magnetic hydrogel spheres, for example, alginate contain the at least one therapeutic agent which upon dissolving of the outer capsule is released from the spheres by diffusion from the alginate. Ferromagnetic microparticle material incorporated into the spheres causes the spheres to maintain proximity to the internal magnet. The magnetic pill is guided by the external magnet to the anatomic location of the target tissue or organ. Hydrogel spheres loaded with a therapeutic agent in the form of nanoparticles are shown in FIG. 5 panel b.

Controlled release of the therapeutic agent in embodiments herein is regulated by the composition and structure of the capsule which for example is manufactured to include an insoluble inner compartment containing the therapeutic agent or nanoparticles and the internal magnet which, for example, is attached with adhesive to the capsule (FIG. 5 panels c and d). The outer cap in this embodiment is soluble and dissolves upon ingestion. Then the therapeutic agent and nanoparticles held within the insoluble inner compartment of the capsule diffuse to the treatment location. Adhesion of the magnet to the capsule prevents loss of the magnet in the subject, such that at termination of therapeutic treatment or exhaustion of the therapeutic agents, the magnet and insoluble inner component of the capsule are guided by the intermagnetic force to site such as an orifice for removal from the subject naturally or by a minimally invasive procedure.

An embodiment of the capsule is manufactured to be generally permeable to at least one or a plurality of therapeutic agents (FIG. 5 panel e), for example, by design of a functionally porous capsule that maintains sufficient structural integrity to contain the internal magnet and is porous for release of low molecular weight therapeutic agents and biological agents such as recombinant proteins. Upon achieving an end-point of treatment, the intact capsule is guided to an orifice for removal from the subject. An embodiment of the capsule is manufactured to include an environmentally-responsive coating that eliminates or retards diffusion of the therapeutic agent for example from nanoparticles, except at a site of the target tissue or organ which has an environment that reacts with the coating to confer permeability and permit diffusion of the agent (FIG. 5 panels f and g). For example, a coating of the magnetic pill is designed to contain a pH-sensitive polymer that remains intact upon ingestion, preventing diffusion of the therapeutic agent or nanoparticles. The pill is guided by the intermagnetic force to the target anatomic location which has the pH at which the pH-sensitive polymer decays or dissolves, rendering the coating permeable. The therapeutic agent for example located in nanoparticles diffuses from the permeablized capsule, thereby constituting a method to regulate rate of release of the therapeutic agent.

An embodiment of the capsule permits passage of the therapeutic agent for example associated with nanoparticles to flow through apertures of the capsule at a regulated rate of release compared to a capsule having a non-permeable surface or to a capsule that is designed to be entirely soluble or semi-soluble, i.e., soluble in a portion of area. Further regulation is obtained by controlling size of the aperture, or manufacturing a capsule to have a plurality of aperture or pore sizes of a series of apertures.

A capsule is manufactured to be insoluble and to include an orifice for releasing a therapeutic-agent, the orifice positioned at an end of the capsule in the outer cap. The orifice controls the rate of release of the therapeutic agent for example contained in nanoparticles (FIG. 5 panels h and i). In various embodiments the orifice has a size in the range of microparticles, for example, about 100 µm to about 250 µm in diameter, for example, from about 1 µm to about 100 µm, from about 1 µm to about 250 µm in diameter, from about 100 µm to about 500 µm, from about 100 µm to about 750 µm or from about 250 µm to about 1000 µm. A capsule having orifices having a size in the range of nanoparticles, such that the orifices permit passage of small molecules are also within the scope of the invention and the capsule is considered to have a coating that is porous and permeable. The orifice shown in FIG. 5 panels h and i is covered by an environmentally-responsive coating such as a pH-sensitive polymer. The therapeutic agent for example included in nanoparticles are passaged or released from the capsule through the orifice, in response to pH or other environmental factors affecting the coating, upon the pill being guided by intermagnetic force to the anatomic location.

An embodiment of the magnetic pill includes an ingestible medical device such as a tumor ablative device and is used to localize treatment to a target tissue or organ in need of radiation treatment or chemotherapy (FIG. 6 panel a). In yet another embodiment, a magnetic pill is used to control delivery of an electrical stimulation to a muscle, a nerve, or the heart to stimulate activity. The device is ingested or placed into a subject, for example by gavage or another surgical method, and is guided to the treatment location and is controlled to initiate stimulation by modulating the inter-magnetic force between the external magnet and the internal magnet.

An embodiment of the magnetic pill includes an osmotic pump device with a water-insoluble coating covering a portion of the device that contains a therapeutic-releasing orifice and a water permeable membrane for controlled-release of at least one therapeutic agent (FIG. 6 panel f). The therapeutic agent contained within the device disperses through the orifice as water passes through the water-permeable membrane.

Compressed magnetic tablets are a homogeneous solid containing at least one therapeutic agent and an internal magnet (FIG. 6 panel b). The tablet dissolves and the agent diffuses at the target anatomic location. Nanoparticles of the therapeutic agent increase bioactivity of the agent at the target tissue or organ (FIG. 6 panel c). An embodiment of the magnetic tablet is manufactured with an insoluble coating that surrounds a portion of the tablet and reduces the tablet's surface area that is exposed to the environment of the target anatomic location (FIG. 6 panels d and e). The rate of solvation of this embodiment of the tablet is redacted compared to a completely soluble tablet.

Figure 7B:
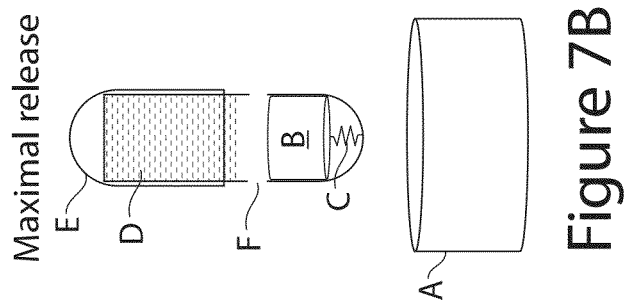
FIG. 7 is a set of drawings of a magnetic pill with a control release regulated by the inter-magnetic force between an internal magnet located in the pill and an external magnet illustrated below the pill. When the inter-magnetic force is low, the therapeutic-releasing orifice remains blocked and prevents release of the therapeutic. When the attractive force is high enough, the spring becomes compressed enabling a diffusion pathway between the therapeutic reservoir and the ambient environment. By cycling inter-magnetic forces, a controlled pulsatile release can be achieved.
Figure 7A:
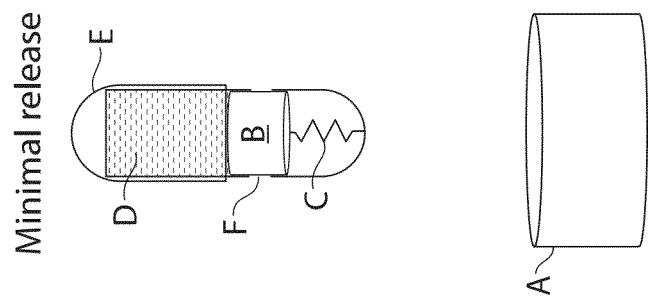

An embodiment of the magnetic pill contains the internal magnet attached to a compressive element such as a spring, which regulates release of the therapeutic agent to the target tissue or organ. The inter-magnetic force between the internal magnet and external magnet regulates opening and closing of a therapeutic releasing orifice of an insoluble capsule. As the force is maintained at a low level, the orifice is closed or blocked by the internal magnet and remains closed (FIG. 7 panel A). Increasing the inter-magnetic force draws the magnet towards the force, compresses the spring and opens the orifice on the pill allowing the therapeutic agents to disperse out of the capsule (FIG. 7 panel B).

Monitoring and controlling a cyclically applied inter-magnetic force between a magnetic oral dose and an external magnet provides the safe and effective localization of a model drug delivery system. Magnetic force monitoring herein reported the inter-magnetic force and distance in real time. Biplanar x-ray fluoroscopy with contrast was used for visualization and quantification of the three dimensional position of the internal magnet in vivo. Co-administration of a radiopaque contrast agent can elucidate more precisely the anatomical position of the magnet at the cost of magnet localization precision. Together, inter-magnetic force monitoring and biplanar fluoroscopic visualization herein provide localized oral drug delivery system with quantitative means of assessing safety and efficacy, in terms of both intestinal tissue damage and localization. Magnetically localized oral drug delivery will be readily applicable to investigating the therapeutic benefit of prolonged local delivery of NAW therapeutics within therapeutic windows, of chemotherapeutics to GI tumors to avoid side effects caused by systemic administration, of nanoencapsulated proteins postulated to achieve increase uptake in certain regions of the small intestines, and of therapeutics for GI diseases enabling administration directly at the site of action.

References

1. Davis, S. S. Drug Discovery Today 10, 249-57 (2005).
2. Chen, H. M., Langer, R. Pharm. Res. 14, 537-540 (1997).
3. Goldberg, M., Gomez-Orellana, I. Nat. Rev. Drug Discovery 2, 289-95 (2003).
4. Langer, R. Nature 392, 5-10 Suppl. S (1998).
5. Mathiowitz, E. et. al. Nature 386, 410-14 (1997).
6. Whitehead, K., Shen, Z. C., Mitragotri, S. J. Controlled Release 98, 37-45 (2004).
7. Arruebo, M., Fernandez-Pacheco, R., Ibarra, M. R., Santamaria, J. Nano Today 2, 22-32 (2007).
8. Groning, R., Bemtgen, M., Georgarakis, M. Eur. J. Pharm. Biophalln. 46, 285-91 (1998).
9. Ito, R., Machida, Y., Sannan, T., Nagai, T. Int. J. Pharm. 61, 109-17 (1990).
10. Polyak, B., Friedman, G. Expert Opin. Drug Delivery 6, 53-70 (2009).
11. Teply, B. A. et al. Biomaterials 29, 1216-1223 (2008).
12. Widder, K. J. et. al. Proc. Natl. Acad. Sci. USA 78, 579-81 (1981).
13. Edelman, E. R., Mathiowitz, E., Langer, R., Klagsbrun, M. Biomaterials 12, 619-26 (1991).
14. Brainerd, E. L. et al. Journal of Experimental Zoology A, 313A (2010).
15. Hedrick, T. L. Bioinspir. Biomim. 3, 6 (2008).
16. Riskin, D. K., et al. J. Theor. Biol. 254, 604-615 (2008).

17. Guignet, R. et al. Neurogastro. and Mot. 18, 472-478 (2006).
18. Laulicht, B. et. al. Proc. Natl. Acad. Sci. USA in press (2010).
19. Ferens, D. M. et al. Neurogastro. and Mot. 17, 714-20 (2005).
20. Shapiro et al, U.S. patent application Ser. No. 12/468,746, published Nov. 19, 2009.

What is claimed is:

1. A method for treating a subject comprising:
administering to an anatomic location of the subject a magnetic pill having: an internal magnet with an internal magnetic force, a drug delivery component and a therapeutic agent; wherein the anatomic location is proximal to a treatment area; and,
applying an external magnet with an external magnetic force to the anatomic location and monitoring an inter-magnetic attractive force between the internal magnet and the external magnet; and
in response to the monitoring, adjusting the inter-magnetic force, wherein the drug delivery component comprises alginate spheres.

2. The method according to claim 1, wherein adjusting comprises at least one of: moving the external magnet, manually shifting the external magnet, electronically shifting the external magnet and removing the external magnet from a vicinity of the internal magnet.

3. The method according to claim 1, wherein the subject comprises a human, a dog, a cat, a rat, a mouse, a primate or other vertebrate species.

4. The method according to claim 1, wherein the alginate spheres comprise calcium alginate or sodium alginate.

5. The method according to claim 1, wherein the internal magnet comprises a magnetic strength of at least about 2 Tesla.

6. The method according to claim 1, wherein the internal magnet comprises at least one component selected from the group consisting of: iron, iron oxide, neodymium iron boron, nickel, aluminum nickel cobalt, cobalt, samarium cobalt, scandium, yttrium, and a lanthanide.

7. The method according to claim 1 wherein the internal magnet has a regular geometrical shape selected from the group consisting of: ellipsoid, cylindrical, ovoid, parallelepiped, slab, and tetrahedral shapes.

8. The method according to claim 1, wherein the internal magnet comprises a corrosion-resistant coating.

9. The method according to claim 8, wherein the coating comprises at least one of chrome and a non-erodible polymer.

10. The method according to claim 1, wherein the therapeutic agent comprises an anesthetic, an antacid, an antibiotic, a bronchial dilator, a detoxifying agent, a diabetes agent, a diuretic, an enzyme, a hormone, an immunosuppressive agent, a narcotic antagonist, an oxytocic, a radiation source, and a respiratory stimulant, or a combination thereof.

11. The method according to claim 1 wherein the magnetic pill comprises at least one of: a tablet, a capsule, an osmotic pump, an electromechanical drug delivery device, a ferromagnetic component, or a combination thereof.

12. The method according to claim 11 wherein the ferromagnetic component is selected from at least one of: iron, iron oxide, neodymium iron boron, nickel, aluminum nickel cobalt, cobalt samarium cobalt, a rare earth element selected from scandium, yttrium, and a lanthanide.

13. The method according to claim 1, wherein the administered magnetic pill contains a radionuclide or tumor ablative device.

14. A method of using a magnetic drug delivery device to deliver a therapeutic agent to an anatomic location of a subject comprising:
orally administering the device to a subject, wherein the device comprises an internal magnetic dose having an internal magnet with an internal magnetic force, a drug delivery component and the therapeutic agent;
applying an external magnet with an external magnetic force and monitoring an inter-magnetic attractive force and distance between the internal magnetic dose and the external magnet;
observing a motion of the internal magnetic dose in real-time using biplanar videofluoroscopy; and,
modulating force exerted on tissue underlying the internal magnet, thereby confirming an anatomic position of the internal magnet and optimizing control of position and force exerted on tissue, thereby delivering the dose to an anatomic location.

15. The method according to claim 14, further comprising during applying the external magnet, monitoring bioavailability and bioactivity of the therapeutic agent using the biplanar videofluoroscopy.

16. The method according to claim 14 wherein the subject comprises a human, a dog, a cat, a rat, a mouse, a primate or other species.

17. The method according to claim 14, wherein the internal magnetic dose delivered to an anatomic location is less than a systemic dose.

18. The method according to claim 14, wherein the agent is an imaging agent.

* * * * *

UNITED STATES PATENT AND TRADEMARK OFFICE
CERTIFICATE OF CORRECTION

| | | |
|---|---|---|
| PATENT NO. | : 8,776,802 B2 | Page 1 of 1 |
| APPLICATION NO. | : 13/217883 | |
| DATED | : July 15, 2014 | |
| INVENTOR(S) | : Mathiowitz et al. | |

It is certified that error appears in the above-identified patent and that said Letters Patent is hereby corrected as shown below:

In the Claims

At column 24, line 13:

delete "cobalt samarium cobalt,"

insert --cobalt, samarium cobalt,--

Signed and Sealed this
Fourteenth Day of October, 2014

Michelle K. Lee
*Deputy Director of the United States Patent and Trademark Office*